United States Patent [19]
Pinkos et al.

[11] Patent Number: 5,463,079
[45] Date of Patent: Oct. 31, 1995

[54] PREPARATION OF FIVE-MEMBERED NITROGEN HETEROCYCLES

[75] Inventors: Rolf Pinkos, Bad Duerkheim; Rolf Fischer, Heidelberg, both of Germany

[73] Assignee: BASF Aktiengesellschaft, Ludwigshafen, Germany

[21] Appl. No.: 266,143

[22] Filed: Jun. 27, 1994

[30] Foreign Application Priority Data

Jul. 1, 1993 [DE] Germany ............... 43 21 843.1

[51] Int. Cl.⁶ .................. C07D 207/263; C07D 207/38; C07D 207/02
[52] U.S. Cl. ................ 548/543; 548/560; 548/565
[58] Field of Search ............................. 548/543

[56] References Cited

U.S. PATENT DOCUMENTS 2,689,263  4/1952  Schmidle et al. ................ 548/543

OTHER PUBLICATIONS

Z. obsc. Chim. English Ed. (1956) pp. 2125–2127.
Synlett. (1991) pp. 693–694.
Journal of the American Chemical Society, (1981) pp. 5969–5972 Trost and Molander.
Tetrahedron Letters (1981), PP. 2557–2578, Tsuji, Jiro, Kataoka, Hideaki, Kobayashi and Yuichi.
Tetrahedron Letters (1981), pp. 195–198, Overman and Flippin.

*Primary Examiner*—David B. Springer
*Attorney, Agent, or Firm*—John H. Shurtleff

[57] ABSTRACT

A process for preparing five-membered nitrogen heterocycles of the general formula I

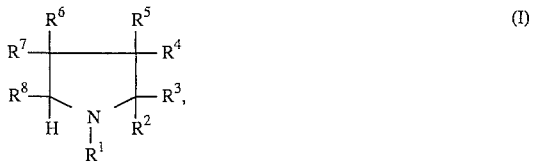

where
$R^1, R^2, R^3, R^4, R^5, R^6, R^7, R^8$ are hydrogen,
$R^1$ is $C_1$–$C_{10}$-alkyl, $C_1$–$C_{10}$-hydroxyalkyl, $C_1$–$C_{10}$-aminoalkyl, aryl, $C_7$–$C_{10}$-aralkyl and $C_7$–$C_{10}$-alkylaryl,
$R^5$ and $R^6$ are $C_1$–$C_8$-alkyl,
$R^2$ and $R^3$ together are oxygen with the proviso that $R^8$ is hydrogen,
$R^3$ and $R^4$ and/or $R^7$ and $R^8$ or $R^4$ and $R^7$ together are a bond,
comprises reacting vinyloxiranes of the general formula II

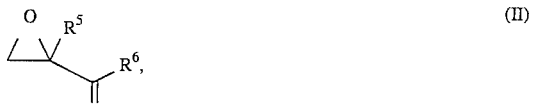

where $R^5$ and $R^6$ have the abovementioned meanings, with ammonia or primary amines of the general formula III

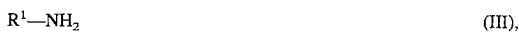

where $R^1$ has the abovementioned meanings, in the presence of a compound of an element of Group VIIIb or Ib of the Periodic Table, with or without the addition of a Lewis acid, at from 20° to 200° C. under from 1 to 70 bar, and subsequently cyclizing in the presence of hydrogen and of a hydrogenation catalyst at from 150° to 350° C. under from 0.1 to 300 bar.

6 Claims, No Drawings

PREPARATION OF FIVE-MEMBERED NITROGEN HETEROCYCLES

The present invention relates to a process for preparing five-membered nitrogen heterocycles by reacting vinyloxiranes with ammonia or primary amines in the presence of a compound of an element of Group VIIIb or Ib of the Periodic Table, and subsequently cyclization in the presence of hydrogen and of a hydrogenation catalyst at elevated temperatures.

U.S. Pat. No. 2,689,263 discloses the ring opening of vinyloxiranes at position 2 with amines in the presence of acid ion exchangers.

Z. obsc. Chim. engl. Edition (1956) 2125–2127 discloses the uncatalyzed ring opening of vinyloxiranes at position 1.

Synlett. (1991) 693–694 discloses the cyclization of the compounds obtained by ring opening with amines using complex ruthenium hydrides in the presence of hydrogen acceptors in the liquid phase.

It is impossible to deduce from the prior art how to prepare compounds of the formula I from vinyloxiranes of the formula II as defined by the structural formulas which follow.

It is an object of the present invention to convert vinyloxiranes of the formula II into compounds of the formula I.

We have found that this object is achieved by a novel process for preparing five-membered nitrogen heterocycles of the general formula I

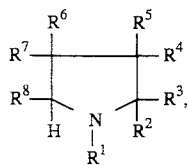

where $R^1, R^2, R^3, R^4, R^5, R^6, R^7, R^8$ are hydrogen, $R^1$ is $C_1$–$C_{10}$-alkyl, $C_1$–$C_{10}$-hydroxyalkyl, $C_1$–$C_{10}$-aminoalkyl, aryl, $C_7$–$C_{10}$-aralkyl and $C_7$–$C_{10}$-alkylaryl, $R^5$ and $R^6$ are $C_1$–$C_8$-alkyl, $R^2$ and $R^3$ together are oxygen with the proviso that $R^8$ is hydrogen, $R^3$ and $R^4$ and/or $R^7$ and $R^8$ or $R^4$ and $R^7$ together are a bond, which comprises reacting vinyloxiranes of the general formula II

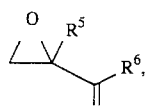

where $R^5$ and $R^6$ have the abovementioned meanings, with ammonia or primary amines of the general formula III

where $R^1$ has the abovementioned meanings, in the presence of a compound of an element of Group VIIIb or Ib of the Periodic Table, with or without the addition of a Lewis acid, at from 20° to 200° C. under from 1 to 70 bar, and subsequently cyclizing in the presence of hydrogen and of a hydrogenation catalyst at from 150° to 350° C. under from 0.1 to 300 bar.

The process according to the invention can be carried out as follows:

The vinyloxiranes II and ammonia or primary amines III can be mixed, where appropriate in an inert solvent, with catalytically effective amounts of a compound of an element of Group VIIIb or Ib of the Periodic Table, with or without the addition of a Lewis acid, and reacted, for example, in a pressure vessel at from 20° to 200° C., preferably 50° to 150° C., particularly preferably 70° to 130° C., under from 1 to 70 bar, preferably 2 to 50 bar, particularly preferably 3 to 30 bar. The reaction mixtures can preferably be worked up, e.g. by distillation, and subsequently the unpurified, but preferably the purified, intermediates can be cyclized under hydrogenating or dehydrogenating conditions using hydrogen, where appropriate in an inert solvent, in the presence of a hydrogenation catalyst in the liquid or gas phase at from 150° to 350° C., preferably 180° to 310° C., particularly preferably 200° to 300° C., under from 0.1 to 300 bar, preferably 5 to 100 bar, particularly preferably 10 to 80 bar.

The cyclization can be carried out batchwise, e.g. in autoclaves, or continuously, e.g. in tubular reactors. The holdup time is, as a rule, from 5 minutes to 3 hours, preferably 10 minutes to 1.5 hours.

The pressure when the cyclization is carried out in the gas phase is, as a rule, from 0.1 to 50 bar, preferably 0.5 to 10 bar.

Examples of suitable solvents for both reactions, the ring opening and the subsequent cyclization, are water or cyclic ethers such as tetrahydrofuran or dioxane.

Suitable catalysts for the ring opening of the vinyloxiranes II are group VIIIb compounds, preferably compounds of palladium in the zero oxidation state, such as tetrakis(triphenylphosphine)palladium(0), bis[1,2-bis(diphenylphosphino)ethane]palladium(0) or dibenzalacetonepalladium(0), particularly preferably tetrakis(triphenylphosphine)palladium(0), or group Ib compounds, preferably copper(I) compounds such as copper(I) fluoride, copper(I) chloride, copper(I) bromide, copper(I) iodide and copper(I) cyanide, particularly preferably copper(I) chloride and bromide.

The ratio by weight of catalysts to vinyloxiranes II is, as a rule, from 0.001:1 to 0.5:1, preferably 0.01:1 to 0.1:1.

Lewis acids can be added as cocatalysts. Examples of these are halides, sulfates or phosphates of elements of Groups Ia, IIa and IIIa and of Groups Ib, IIb and IIIb of the Periodic Table, such as LiF, LiCl, $CuCl_2$, $ZnSO_4$, $ZnCl_2$ and $Al_2(SO_4)_3$.

The ratio by weight of the cocatalysts to the vinyloxiranes II may, as a rule, be from 0.005:1 to 0.5:1, preferably 0.01:1 to 0.4:1.

Preferred compounds III are ammonia, methylamine, ethylamine, ethanolamine and aniline.

The molar ratio of the compounds III to the vinyloxiranes II is, as a rule, from 0.5:1 to 150:1, preferably 1:1 to 100:1, particularly preferably 2:1 to 50:1.

The mixture of products can be worked up, for example, by distillation. It is possible in this way to remove excess amine and, where appropriate, unreacted vinyloxirane II for recycling. Compounds of the formulae IVb and IVc

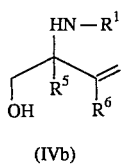
(IVb)

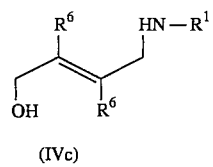
(IVc)

can be separated from compounds of the formula IVa

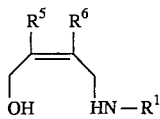
(IVa)

by distillation. Compounds of the formulae IVb and c can, in order to increase the overall selectivity, be rearranged by conventional methods to compounds of the formula IVa (e.g. as described in Bull. Chem. Soc. France (1965) 2082–2089).

Suitable hydrogenation catalysts are those able to catalyze the hydrogenation of ketones or aldehydes with hydrogen to alcohols. Examples thereof are described in Houben-Weyl, Methoden der organischen Chemie, Volume IV/1c, Georg Thieme Verlag Stuttgart, pages 16–44 (1980), such as elements of Groups Ib and VIb to VIIIb of the Periodic Table, e.g. in the form of the metals or their oxides and sulfides. They can be employed, for example, as supported catalysts, skeleton catalysts, black catalysts or mixed metal catalysts. Examples are Pt black, Pt/C, Pt/$Al_2O_3$, $PtO_2$, Pd black, Pd/C, Pd/$Al_2O_3$, Pd/$SiO_2$, Pd/$CaCO_3$, Pd/$BaSO_4$, Rh/C, Rh/$Al_2O_3$, Ru/$SiO_2$, Ni/$SiO_2$, Raney nickel, Co/$SiO_2$, Co/$Al_2O_3$, Raney cobalt, Fe, iron-containing mixed catalysts, Re black, Raney rhenium, Cu/$SiO_2$, Cu/$Al_2O_3$, Raney copper, Cu/C, $PtO_2$/$Rh_2O_3$, Pt/Pd/C, $CuCr_2O_4$, $BaCr_2O_4$, Ni/$Cr_2O_3$/$Al_2O_3$, $Re_2O_7$, CoS, NiS, $MoS_3$, Cu/$SiO_2$/$MoO_3$/$Al_2O_3$. Preferred catalysts contain Cu as component.

The substituents $R^1$, $R^2$, $R^3$, $R^4$, $R^5$, $R^6$, $R^7$ and $R^8$ in the compounds I, II, III and IVa to c have the following meanings:

$R^1, R^2, R^3, R^4, R^5, R^6, R^7, R^8$
hydrogen, $R^1$
$C_1$–$C_{10}$-alkyl, preferably $C_1$–$C_8$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, n-heptyl, isoheptyl, n-octyl, isooctyl, particularly preferably $C_1$–$C_4$-alkyl such as methyl, ethyl, n-propyl, isopropyl, n-butyl, isobutyl, sec-butyl and tert-butyl, $C_1$–$C_{10}$-hydroxyalkyl, preferably $C_1$–$C_8$-hydroxyalkyl, particularly preferably $C_1$–$C_4$-hydroxyalkyl such as hydroxymethyl, 1-hydroxyethyl, 2-hydroxyethyl, 1-hydroxy-n-propyl, 2-hydroxy-n-propyl, 3-hydroxy-n-propyl and 1-hydroxy-1-methylethyl, $C_1$–$C_{10}$-aminoalkyl, preferably $C_1$–$C_8$-aminoalkyl, particularly preferably $C_1$–$C_4$-aminoalkyl such as aminomethyl, 1-aminoethyl, 2-aminoethyl, 1-amino-n-propyl, 2-amino-n-propyl, 3-amino-n-propyl and 1-amino-1-methylethyl, aryl such as phenyl, $C_7$–$C_{10}$-aralkyl, preferably $C_7$–$C_9$-phenylalkyl such as benzyl, 1-phenethyl, 2-phenethyl, 1-phenylpropyl, 2-phenylpropyl and 3-phenylpropyl, particularly preferably benzyl, 1-phenethyl and 2-phenethyl, $C_7$–$C_{10}$-alkylaryl, preferably $C_7$–$C_9$-alkylphenyl such as 2-methylphenyl, 3-methylphenyl, 4-methylphenyl, 2,4-dimethylphenyl, 2,5-dimethylphenyl, 2,6-dimethylphenyl, 3,4-dimethylphenyl, 3,5-dimethylphenyl, 2,3,4-trimethylphenyl, 2,3,5-trimethylphenyl, 2,3,6-trimethylphenyl, 2,4,6-trimethylphenyl, 2-ethylphenyl, 3-ethylphenyl, 4-ethylphenyl, 2-n-propylphenyl, 3-n-propylphenyl and 4-n-propylphenyl, $R^5$ and $R^6$
$C_1$–$C_8$-alkyl, preferably $C_1$–$C_4$-alkyl such as methyl, ethyl, n-propyl, isopropyl, n-butyl, isobutyl, sec-butyl and tert-butyl, particularly preferably methyl and ethyl, $R^2$ and $R^3$
together oxygen with the proviso that $R^8$ is hydrogen, and $R^3$ and $R^4$ and/or $R^7$ and $R^8$ or $R^4$ and $R^7$ together a bond.

The five-membered nitrogen heterocycles are suitable, for example, as solvents or synthons for synthesizing active compounds.

EXAMPLES

Example 1

10 g of vinyloxirane, 25 g of methylamine and 0.6 g of Pd(PPh$_3$)$_4$ in a glass pressure vessel were heated in an oil bath at 60° C. for 1 h. The pressure in the reaction vessel rose to about 15 bar, and was 9 bar at the end of the reaction. The reaction mixture contained after removal of the excess methylamine 33% 1-hydroxy-4-methylamino-2-butene, 39% 1-hydroxy-2-methylamino-3-butene and 3% 2-hydroxy-1-methylamino-3-butene.

Example 2

1 g of vinyloxirane, 4.6 g of methylamine, 0.1 g of Pd(PPh$_3$)$_4$, 0.1 g of ZnCl$_2$ and 0.02 g of LiI were reacted as in Example 1. The reaction mixture contained after removal of the excess methylamine 30% 1-hydroxy-4-methylamino-2-butene and 57% 1-hydroxy-2-methylamino-3-butene.

Example 3

23 g of vinyloxirane, 107 g of methylamine, 2.7 g of Pd(PPh$_3$)$_4$, 0.5 g of LiI and 2.5 g of ZnCl$_2$ were reacted as in Example 2. The reaction was complete after 10 minutes. The reaction mixture contained after removal of the excess methylamine 37% 1-hydroxy-4-methylamino-2-butene and 52% 1-hydroxy-2-methylamino-3-butene. The mixture was subjected to short-path distillation under 0.1 mbar at a bottom temperature of 95° C. 26 g of a colorless oil were obtained and were redistilled through a 30 cm column. The top product obtained at 39°–45° C. under 0.1 mbar comprised 15 g of 96% pure 1-hydroxy-2-methylamino-3-butene. The bottom product comprised about 11 g of 98% pure 1-hydroxy-4-methylamino-2-butene.

Example 4

5.5 g of 1-hydroxy-4-methylamino-2-butene and 3 g of a CuO (10%)/active carbon catalyst which had been activated with hydrogen were introduced into a 50 ml metal autoclave. After injection of 50 bar of hydrogen, the mixture was heated at 250° C. for 1 h. After cooling and decompression, the reaction mixture contained 50% N-methylpyrrolidine, 15% N-methylpyrrole and 1% N-methylpyrrolidone.

Example 5

20 ml/h of a 10% by weight solution of 1-hydroxy-4-methylamino-2-butene in tetrahydrofuran were passed over a Cu/SiO$_2$ catalyst (11% CuO, 7% CaO, 1% Na$_2$O on SiO$_2$) at 250° C. and 1013 mbar in a stream of hydrogen (10 l/h). The reaction mixture contained 65% N-methylpyrrolidine, 25% N-methylpyrrole and 10% N-methylpyrrolidone.

We claim:

1. A process for preparing five-membered nitrogen heterocycles of the general formula I

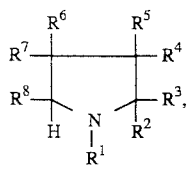  (I)

where, independently of each other, $R^1$, $R^2$, $R^3$, $R^4$, $R^5$, $R^6$, $R^7$ and $R^8$ may each represent hydrogen, $R^1$ is also C$_1$–C$_{10}$-alkyl, C$_1$–C$_{10}$-hydroxyalkyl, C$_1$–C$_{10}$-aminoalkyl, aryl, C$_7$–C$_{10}$-aralkyl or C$_7$–C$_{10}$-alkylaryl, where taken together, $R^2$ and $R^3$ may further represent oxygen with the proviso that $R^8$ is hydrogen, and each of the paired substituents $R^3$ and $R^4$, $R^7$ and $R^8$ and $R^4$ and $R^7$ may each represent a bond with the proviso that $R^4$ and $R^7$ do not represent said bond when one or both of the other two paired substituents represent said bond, which process comprises:

reacting a vinyloxirane of the general formula II

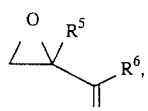  (II)

where R$^5$ and R$^6$ have the abovementioned meanings, with ammonia or a primary amine of the general formula III $$R^1\text{—NH}_2 \quad \text{(III),}$$

where R$^1$ has the abovementioned meanings, in the presence of a compound of an element of Group VIIIb or Ib of the Periodic Table, with or without the addition of a Lewis acid, at a temperature from 20° to 200° C. and under a pressure from 1 to 70 bar, and subsequently cyclizing in the presence of hydrogen and a hydrogenation catalyst at temperatures from 150° to 350° and under pressures from 0.1 to 300 bar.

2. A process for preparing five-membered nitrogen heterocycles I as claimed in claim 1, wherein $R^1$ is hydrogen or methyl, $R^2$, $R^3$, $R^4$, $R^5$, $R^6$, $R^7$ and $R^8$ are hydrogen or $R^2$ and $R^3$ together are oxygen or $R^3$ and $R^4$ and $R^7$ and $R^8$ or $R^4$ and $R^7$ together are a bond.

3. A process for preparing five-membered nitrogen heterocycles I as claimed in claim 1, wherein complex compounds of palladium in the zero oxidation state or copper(I) salts are employed as the first step catalyst.

4. A process for preparing five-membered nitrogen heterocycles I as claimed in claim 1, wherein metal Group Ib or VIb to VIIIb of the Periodic Table are employed as hydrogenation catalysts in the second step.

5. A process for preparing five-membered nitrogen heterocycles I as claimed in claim 1, wherein elements of Group Ib or VIb to VIIIb of the Periodic Table are employed in the form of their metals or their oxides or sulfides as hydrogenation catalysts in the second step.

6. A process for preparing five-membered nitrogen heterocycles I as claimed in claim 5, wherein copper-containing catalysts are employed.

\* \* \* \* \*

UNITED STATES PATENT AND TRADEMARK OFFICE
CERTIFICATE OF CORRECTION

PATENT NO. : 5,463,079
DATED : October 31, 1995
INVENTOR(S) : Pinkos et al.

It is certified that error appears in the above-identified patent and that said Letters Patent is hereby corrected as shown below:

Col. 3, lines 1-6, formula (IVc) should read:

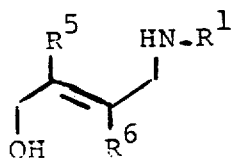

Col. 6, Claim 4, line 27,:
after "wherein" change "metal" to --metals-- and insert --of-- before "Group".

Col. 5, Claim 1, line 23:
after "$C_7$-$C_{10}$-alkylaryl," add --and $R^5$ and $R^6$ are also $C_1$-$C_8$-alkyl; and --

Signed and Sealed this

Thirtieth Day of January, 1996

Attest:

BRUCE LEHMAN

Attesting Officer

Commissioner of Patents and Trademarks